United States Patent [19]

Wagemann et al.

[11] 4,451,932
[45] Jun. 5, 1984

[54] INFANT RESTRAINT

[76] Inventors: Dolores M. Wagemann, 24663 E. 6th St.; Connie S. Myers, 7380 Guthrie St., both of San Bernardino, Calif. 92410

[21] Appl. No.: 446,465

[22] Filed: Dec. 3, 1982

[51] Int. Cl.³ ............................................. A61F 13/00
[52] U.S. Cl. .......................................... 2/80; 128/133
[58] Field of Search ................. 2/80, 1, 102; 128/133, 128/134

[56] References Cited

U.S. PATENT DOCUMENTS

| 1,944,451 | 1/1934 | Newman | 128/134 |
| 2,828,738 | 4/1958 | Strelakos | 128/133 |
| 3,082,764 | 3/1963 | Galanis | 128/133 |

Primary Examiner—Doris L. Troutman
Attorney, Agent, or Firm—Jack C. Munro

[57] ABSTRACT

A restraint assembly for an infant, and particularly for a premature infant, which takes the form of a shirt or vest which is to cover the torso of the infant from which extends sleeves to be located about each arm of the infant. Each sleeve is to be closable by a closing flap preventing the infant's hands from extending exteriorly of the sleeve. The vest includes a closable center opening located across the chest of the infant. The straps are to be securable to each sleeve and are to be secured to an exterior structure, such as the table on which the infant is located. Booties are to be provided which are located about each foot of the infant. The outer end of each bootie is openable and closable also through the use of a closing flap. Securing straps are also to be secured to each bootie. A hood is to be located about the head of the infant. The hood is to be removably secured to the vest.

7 Claims, 4 Drawing Figures

U.S. Patent    Jun. 5, 1984    4,451,932
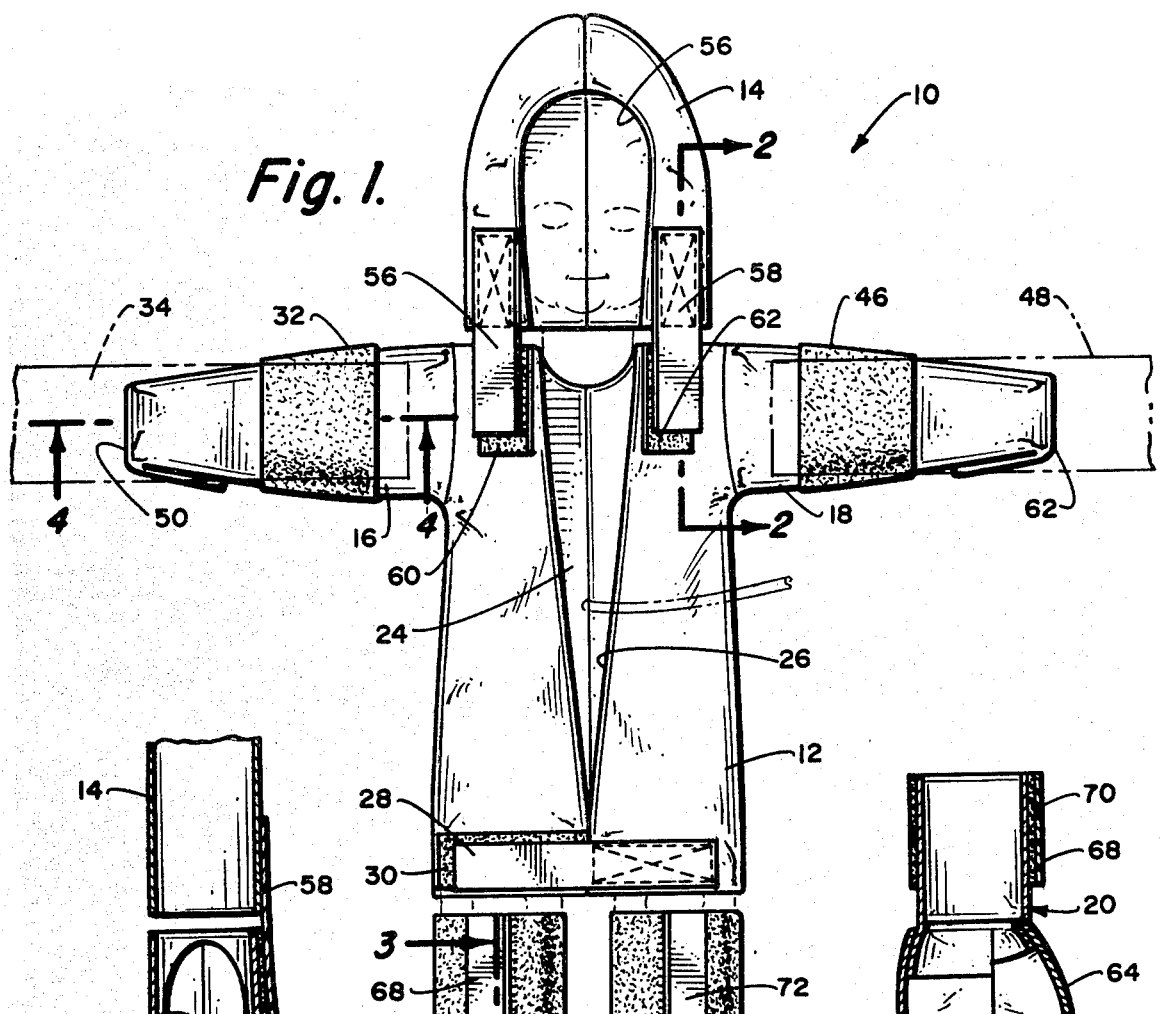
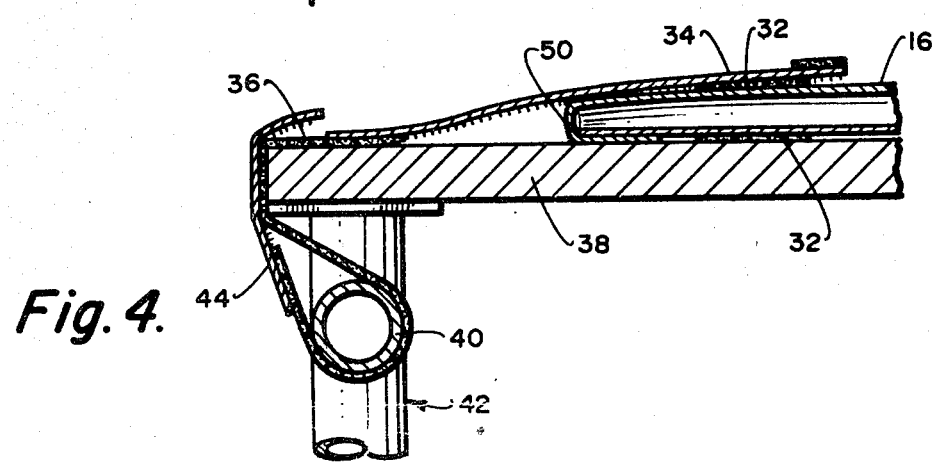

INFANT RESTRAINT

BACKGROUND OF THE INVENTION

The field of this invention relates to wearing apparel, and more particularly to wearing apparel for use by a newborn, premature infant.

Newborn infants are normally placed in a basinette or crib in a comfortably warm environment. Premature infants are normally not clothed. Even though the infant is located in a warm environment, the unclothed infant is subjected to drafts which can cause chills. Premature infants are extremely sensitive and possibly any chill could result in the infant catching a cold which could be quite serious. Also with premature infants, there is normally a continuous stream of medical procedures required on a daily basis. Examples of these medical procedures are the taking of blood, giving injections and the introduction of an I.V. into the umbilicus of the infant. The insertion of an I.V. within the umbilicus of the infant can be a dangerous procedure.

There is a need for finding some means to restrain the infant during the performing of different medical procedures. There is also a need to provide some type of clothing for the infant to supply additional warmth to the infant to prevent chilling.

SUMMARY OF THE INVENTION

An infant restraint assembly which is constructed of a plurality of different parts. The main part comprises a vest or shirt, which is to be located about the torso of the infant. The vest is open at the front (down the chest of the infant) so as to facilitate access of I.V. tubes to the umbilicus of the infant, locating of a stethoscope on the chest of the infant and also to facilitate the performing of other medical procedures to the chest and umbilicus of the infant. The vest is integrally connected to a pair of sleeves. An arm of the infant is to be located within each sleeve. In order to facilitate retaining of warmth, each sleeve is to be closable by a closing flap. The flap is to be movable so as to permit access to the fingers of the infant, again for the performing of desirable medical procedures. Each sleeve has mounted thereon one portion of a fastener assembly. Each fastener assembly is to be connected to a strap, with there being two in number of straps utilized. Each strap is to connect with a separate fixed structure thereby restraining each arm of the infant. The vest is to be closable about the open front by means of a separate fastener assembly. A hood is to be located about the head of the infant, with the hood being connectable through yet another fastener assembly to the vest. A bootie is to be located about the foot of each foot of the infant. Each bootie is enclosed at its outermost end by means of a closing flap. The closing flap is to facilitate access to the toes of the infant, again for the performing of desirable medical procedures. Each bootie is connected to a portion of yet another fastener assembly, with these portions to be connected to separate straps, which in turn are to be attached to a fixed structure to thereby restrain leg movement of the infant.

The primary objective of the present invention is to construct a restraint assembly for an infant, in which the extremities of the infant are restrained against movement so as to substantially unhinder the performing of medical procedures upon the infant.

Another objective of this invention is to construct a restraint assembly which further functions as a article of clothing to protect the infant against loss of body heat.

Another objective of this invention is to construct a restraint assembly for an infant which can be constructed to be reusable or can be constructed to be disposable.

Another objective of this invention is to construct a restraint assembly for an infant which can be manufactured relatively inexpensively.

BRIEF DESCRIPTION OF THE DRAWING

FIG. 1 is a frontal view depicting a premature infant upon which has been located the restraint assembly of the present invention;

FIG. 2 is a cross-sectional view taken along line 2—2 of FIG. 1 showing the connection between the hood and the vest;

FIG. 3 is a cross-sectional view taken along line 3—3 of FIG. 2 showing the internal construction of a bootie; and FIG. 4 is a cross-sectional view taken along line 4—4 of FIG. 1 showing the internal construction of a sleeve and its connecting strap.

DETAILED DESCRIPTION OF THE SHOWN EMBODIMENT

Referring particularly to the drawing, there is shown the restraint assembly 10 of this invention which is constructed generally of a vest 12, a hood 14, sleeves 16 and 18 and booties 20 and 22. The vest 12, hood 14, sleeves 16 and 18 and booties 20 and 22 are to be constructed of a fabric material, such as a soft cotton. However, the material of construction is deemed to be whatever is preferable and in certain instances, the material of construction could be of such a nature as to facilitate single usage and then disposal of the restraint assembly. However, normally the fabric will be such that it can be reused and sterilized without incurring any damage.

The vest 12 is constructed to wrap around the toros 24 of the infant. The vest 12 is open at the front or down the torso 24 forming a V-shaped gap 26. A disengageable and re-engageable fastener assembly, such as strips 28 and 30, are to be utilized to affect holding together of the portions of the vest 12 located on either side of the opening 26. Strip 30 is mounted on the vest 12 on one side of the opening 26, with the strip 28 being attached to the vest 12 on the opposite side of the opening 26. The strip 28 will include a mass of tiny protruding hooks, with the strip 30 including a mass of tiny protruding eyelets. The strip 28 attached to the strip 30 give an extremely secure connection therebetween. This type of fastener assembly is deemed to be conventional and is normally marketed under the trademark of "Velcro". It is considered to be within the scope of this invention that other desirable types of removable fasteners could be utilized without departing from the scope of this invention.

The sleeve 16 is integrally connected to the vest 12 and has mounted thereon a strip 32 which is similar to strip 30. Strip 32 is to engage with a strip 34 which is similar to the strip 28. The strip 34 functions as a strap with its free end thereof being similarly connected to a strip 36. The strip 36 is to extend about an edge of the mattress 38 upon which the infant rests and is to be located about brace 40 of the crib 42. Attached to the outer end of the strip 36 is a strip 44 which is similar to the strip 28. Strip 44 is to engage with a section of the strip 36.

It can thus be seen that with the strip 34 engaging with the strip 32 and the strip 36 extending about the brace 40 with the strip 44 engaging with a portion of strip 36, the sleeve 16 is secured and therefore restrains the arm of the infant which is located within the sleeve 16. A similar restraint arrangement is utilized in conjunction with the sleeve 18 between the strip 46 attached to the sleeve 18 and the strip 48 which is to function as the strap to secure to the portion of the particular type of table the infant is placed upon 42.

The outer end of the sleeve 16 is open but is normally closed by a flap 50. The flap 50 includes a pocket which is integrally formed with the sleeve 16 and is merely folded over about the outer open end of the sleeve 16. This flap can be folded back to facilitate access to the hand and fingers of the infant in order to perform a medical examination of medical procedure. It is to be understood that the sleeve 18 will similarly include a closing flap 52.

The hood 14 includes an opening 56 which is to provide access for the face of the infant. The hood 14 has attached thereto straps 56 and 58 which are similar to the strip 28. The straps 56 and 58 are to connect with respectively with strips 60 and 62. The strip 60 is fixedly mounted to the vest 12 on one side of the opening 26, with the strip 62 being mounted to the vest 12 on the other side of the opening 26.

Each of the booties 20 and 22 are constructed of two parts, such as parts 64 and 66 of bootie 20. The parts 64 and 66 are to overlap each other to thereby close the outer extremity of the bootie 20. However, the part 64 can be separated from the part 66 to facilitate access to the feet and toes of the infant for the performing of medical procedures or examinations.

Mounted on leg band section of the bootie 20 is a strip 68 which is similar to strip 28 and a strip 70 which is similar to strip 30. Therefore, once the bootie 20 is located in position on the infant's leg, the strip 68 is engaged with the strip 70 thereby securing the bootie 20 onto the leg of the infant.

Attached to the leg band section of the bootie 22 are strips 72 and 74 which are similar to strips 68 and 70. It is to be understood that one edge of the strip 72 is integrally secured to an edge of the strip 74. Similarly, one edge of the strip 68 is integrally secured to an edge of the strip 70.

The strips 70 and 74 are each to be connectable to a separate connecting strap which is similar to straps 34 and 48. These straps will in turn connect to fixed portions of the particular type of table the infant is on, such as brace 40 so as to restrain the infant's legs against movement.

What is claimed is:

1. In combination with an infant, said infant having a torso from which extends a head, legs and arms, with a foot connected to each leg, a restraint assembly for substantially immobilizing said infant, said restraint assembly comprising:
   a vest to be located about said torso, said vest including an opening assembly for permitting ease of accessability to the torso, a disengageable first fastener assembly attached to said vest directly adjacent said opening assembly, said first fastener assembly to be operable to connect together said vest about said opening assembly;
   a pair of sleeves attached to said vest and extending therefrom, a said arm to extend through a said sleeve, a first pair of securing straps removably connected by a second fastener assembly to said sleeve; and
   a bootie for each said foot, a second pair of securing straps removably connected by a third fastening assembly to said booties, whereby both said first pair and said second pair of securing straps are to be connected to a separate structure thereby restraining said infant.

2. The combination as defined in claim 1 wherein:
said opening assembly comprising a gap located across the chest of the infant.

3. The combination as defined in claim 2 wherein:
each said sleeve having an outer end, said outer end being closable by a first closing flap.

4. The combination as defined in claim 2 wherein:
each said bootie having an outer end, said outer end of each said bootie being closable by a second closing flap.

5. The combination as defined in claim 3 wherein:
each said bootie having an outer end, said outer end of each said bootie being closable by a second closing flap.

6. The combination as defined in claim 5 including:
a hood to be located about the head of the infant, said hood being connected to a pair of attaching straps, said attaching straps to removably engage with said vest.

7. The combination as defined in claim 1 wherein:
a hood to be located about the head of the infant, said hood being connected to a pair of attaching straps, said attaching straps to removably engage with said vest.

* * * * *